US011452612B2

(12) United States Patent
Stinchfield et al.

(10) Patent No.: US 11,452,612 B2
(45) Date of Patent: Sep. 27, 2022

(54) SPINAL IMPLANT SYSTEM AND METHOD

(71) Applicant: Warsaw Orthopedic, Inc., Warsaw, IN (US)

(72) Inventors: Thomas J. Stinchfield, Germantown, TN (US); Jonathan M. Dewey, Memphis, TN (US); Julien J. Prevost, Memphis, TN (US); Erick Vasquez, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/122,618

(22) Filed: Sep. 5, 2018

(65) Prior Publication Data

US 2019/0000645 A1 Jan. 3, 2019

Related U.S. Application Data

(63) Continuation-in-part of application No. 15/957,346, filed on Apr. 19, 2018, now Pat. No. 10,624,759, and a continuation of application No. 14/510,895, filed on Oct. 9, 2014, now Pat. No. 9,974,663.

(51) Int. Cl.
*A61F 2/44* (2006.01)
*A61F 2/30* (2006.01)

(52) U.S. Cl.
CPC .............. *A61F 2/4465* (2013.01); *A61F 2/44* (2013.01); *A61F 2002/30507* (2013.01); *A61F 2002/30537* (2013.01); *A61F 2002/30538* (2013.01); *A61F 2002/30556* (2013.01); *A61F 2002/30579* (2013.01); *A61F 2002/30601* (2013.01)

(58) Field of Classification Search
CPC .................... A61F 2/44–447; A61F 2/4601
See application file for complete search history.

(56) References Cited

U.S. PATENT DOCUMENTS

| 5,236,460 | A | * | 8/1993 | Barber | ................... | A61F 2/441 |
| | | | | | | 403/109.7 |
| 5,989,280 | A | | 11/1999 | Biedermann et al. | | |
| 5,989,290 | A | | 11/1999 | Biedermann et al. | | |
| 6,015,436 | A | | 1/2000 | Schoenhoeffer | | |

(Continued)

OTHER PUBLICATIONS

International Search Report and Written Opinion for PCT/US2015/054125 the counter part application dated Jan. 18, 2016, 11 pages.

(Continued)

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A method of treating a spine includes implanting a spinal implant within a patient. The spinal implant includes a first member having a first wall defining an axial passageway and a first opening, the first opening being in communication with the axial passageway. A second member includes a second wall defining an axial channel having the first member disposed therein, the second wall defining a second opening in communication with the axial channel. Bone graft is injected through the first opening and into the axial passageway and through the second opening and into the axial channel after the spinal implant is implanted within the patient.

19 Claims, 15 Drawing Sheets

(56) References Cited

U.S. PATENT DOCUMENTS

| | | | |
|---|---|---|---|
| 6,176,861 B1 | 1/2001 | Schaer et al. | |
| 6,193,756 B1 | 2/2001 | Studer et al. | |
| 6,344,057 B1* | 2/2002 | Rabbe | A61F 2/30744 623/17.11 |
| 6,730,088 B2* | 5/2004 | Yeh | A61F 2/44 606/247 |
| 6,866,682 B1 | 3/2005 | An et al. | |
| 6,908,485 B2 | 6/2005 | Crozet et al. | |
| 7,056,343 B2* | 6/2006 | Schafer | A61F 2/44 623/17.11 |
| 7,674,296 B2 | 3/2010 | Roda et al. | |
| 7,811,327 B2* | 10/2010 | Hansell | A61F 2/44 623/17.14 |
| 8,062,366 B2 | 11/2011 | Melkent | |
| 8,211,178 B2* | 7/2012 | Melkent | A61F 2/44 623/17.16 |
| 8,282,683 B2* | 10/2012 | McLaughlin | A61F 2/4455 623/17.11 |
| 9,974,663 B2* | 5/2018 | Stinchfield | A61F 2/4465 |
| 10,292,832 B2* | 5/2019 | Sutterlin, III | A61F 2/4465 |
| 2005/0240267 A1* | 10/2005 | Randall | A61F 2/44 623/17.11 |
| 2006/0100710 A1* | 5/2006 | Gutlin | A61F 2/44 623/17.15 |
| 2006/0293755 A1* | 12/2006 | Lindner | A61F 2/442 623/17.15 |
| 2008/0039948 A1* | 2/2008 | Biedermann | A61F 2/44 623/17.16 |
| 2008/0167720 A1* | 7/2008 | Melkent | A61F 2/4637 606/279 |
| 2008/0281424 A1* | 11/2008 | Parry | A61F 2/4455 623/17.16 |
| 2009/0138089 A1 | 5/2009 | Doubler et al. | |
| 2009/0164017 A1 | 6/2009 | Sommerich et al. | |
| 2010/0179655 A1* | 7/2010 | Hansell | A61F 2/44 623/17.11 |
| 2010/0204794 A1* | 8/2010 | Jarzem | A61B 17/8805 623/17.12 |
| 2011/0004307 A1* | 1/2011 | Ahn | A61F 2/4455 606/279 |
| 2012/0265303 A1* | 10/2012 | Refai | A61F 2/44 623/17.11 |
| 2013/0123921 A1* | 5/2013 | Jones | A61F 2/4601 623/16.11 |
| 2014/0107787 A1 | 4/2014 | Stinchfield et al. | |
| 2014/0142706 A1 | 5/2014 | Hansell et al. | |
| 2014/0207236 A1 | 7/2014 | Prevost et al. | |
| 2014/0277510 A1* | 9/2014 | Robinson | A61F 2/447 623/17.16 |
| 2015/0018957 A1* | 1/2015 | Nichols | A61F 2/44 623/17.16 |
| 2015/0032210 A1* | 1/2015 | Stinchfield | A61F 2/4455 623/17.16 |
| 2016/0100955 A1 | 4/2016 | Stinchfield et al. | |
| 2018/0235773 A1 | 8/2018 | Stinchfield et al. | |

OTHER PUBLICATIONS

PCT/US2019/048077 International Search Report and Written Opinion of the International Searching Authority dated Dec. 13, 2019 from Korean Patent Office.

European Patent Office, 80298 Munich, Germany, Extended European Search Report, Application No. 19856860.20, Applicant: Warsaw Orthopedic, Inc., dated Aug. 5, 2022.

* cited by examiner

SPINAL IMPLANT SYSTEM AND METHOD

CROSS REFERENCE TO RELATED APPLICATIONS

This application is a continuation-in-part of and claims priority to co-pending U.S. patent application Ser. No. 15/957,346, filed Apr. 19, 2018, which is a continuation of and claims priority to U.S. patent application Ser. No. 14/510,895, filed on Oct. 9, 2014. These applications are expressly incorporated herein by reference, in their entireties.

TECHNICAL FIELD

The present disclosure generally relates to medical devices and methods for the treatment of musculoskeletal disorders, and more particularly to a surgical system that includes a spinal implant and a method for treating a spine by pre-packing and post-packing the spinal implant with bone graft all at one time.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants, such as, for example, expandable cages to restore the mechanical support function of vertebrae. The expandable cages may be packed with bone graft to promote fusion. The current method for packing bone graft into an expandable cage is a two-step process. First, the cage is pre-packed on the back table by the surgeon or sometimes by the assistant. Second, once the cage is inserted, expanded and locked into its final position, the surgeon will post-pack the cage in-situ. Depending on the system, there are different options for post-packing including funnels, syringes, or transferring the graft using a pick-up tool and packing it tight with a bone tamp. This process can be both time consuming and frustrating, as it can be difficult to cram either small pieces of bone or messy allograft through small holes. This disclosure describes an improvement over these prior art technologies.

SUMMARY

In one embodiment, a method of treating a spine comprises the steps of implanting a spinal implant within a patient, the spinal implant comprising: a first member comprising a first wall defining an axial passageway and a first opening, the first opening being in communication with the axial passageway, a second member including a second wall defining an axial channel having the first member disposed therein, the second wall defining a second opening in communication with the axial channel; and injecting bone graft through the first opening and into the axial passageway and through the second opening and into the axial channel after the spinal implant is implanted within the patient.

In one embodiment, a method of treating a spine comprises the steps of implanting a spinal implant within a patient, the spinal implant comprising: an outer body defining an axial cavity and a first port in communication with the axial cavity, and an inner body positioned in the axial channel and defining an axial passageway and a second port in communication with the axial passageway, and injecting bone graft through the first port and into the axial cavity and through the second port and into the axial passageway after the spinal implant is implanted within the patient, wherein the spinal implant is free of bone graft prior to being implanted within the patient.

In one embodiment, a method of treating a spine comprises the steps of: implanting a spinal implant within a patient, the spinal implant comprising: an outer body defining an axial cavity extending through opposite top and bottom end surfaces of the outer body and a first port in communication with the axial cavity, an inner body positioned in the axial channel and defining an axial passageway extending through opposite top and bottom end surfaces of the outer body and a second port that is communication with the axial passageway, and a cap that removably engages the inner body such that the cap is rotatable relative to the inner body, the cap defining an axial channel extending through opposite top and bottom end surfaces of the cap; and injecting bone graft into the spinal implant by positioning a tip of a first delivery instrument into the first port and injecting bone graft through the first port and into the axial cavity and positioning a tip of a second delivery instrument in the second port and injecting bone graft through the second port and into the axial passageway, wherein the first port has a diameter that matches a diameter of the tip of the first delivery instrument and the second port has a diameter that matches a diameter of the tip of the second delivery instrument, and wherein the spinal implant is free of bone graft prior to being implanted within the patient.

BRIEF DESCRIPTION OF THE DRAWINGS

The present disclosure will become more readily apparent from the specific description accompanied by the following drawings, in which.

DETAILED DESCRIPTION

Figure 1:
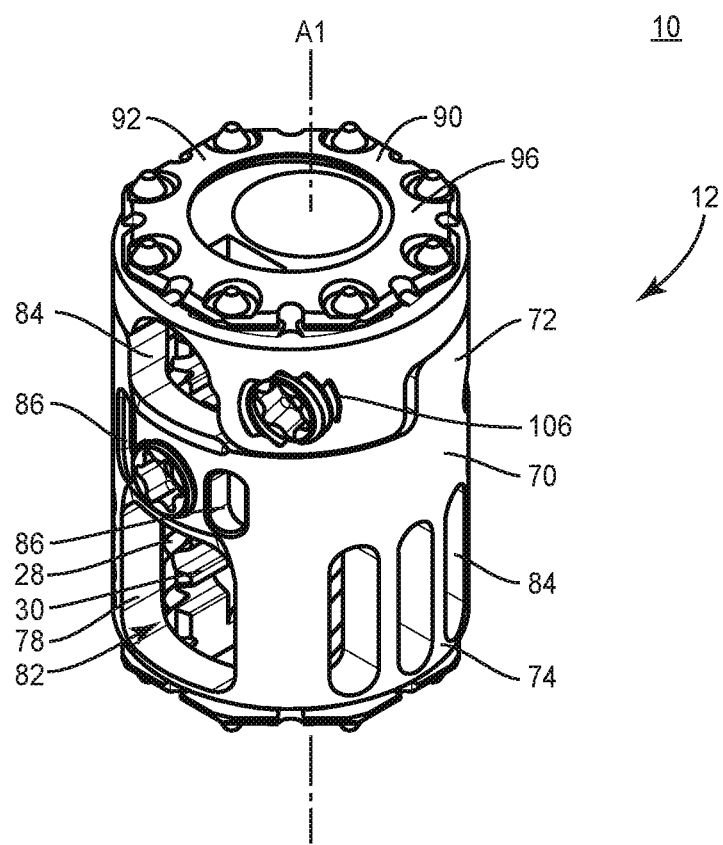
FIG. 1 is a perspective view of components of one embodiment of a surgical system in accordance with the principles of the present disclosure.
Figure 2:
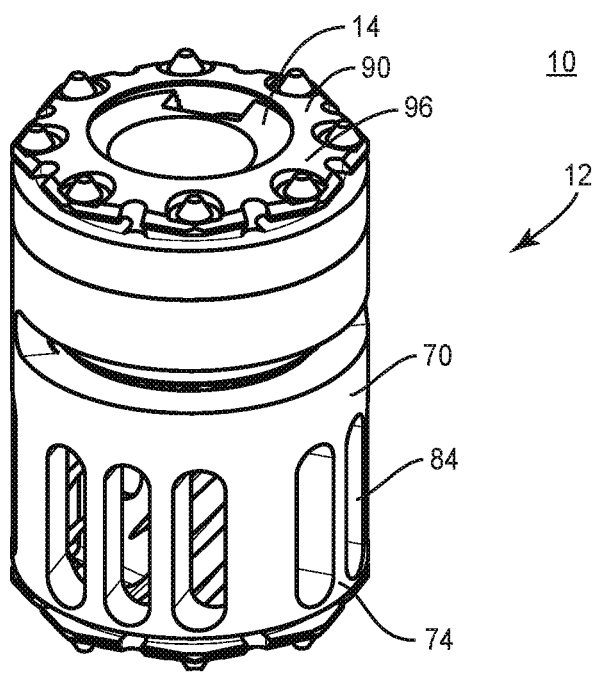
FIG. 2 is a perspective of the components shown in FIG. 1.

The exemplary embodiments of the surgical system and related methods of use disclosed are discussed in terms of medical devices for the treatment of musculoskeletal disorders and more particularly, in terms of a surgical system that includes a spinal implant and a method for treating a spine.

In some embodiments, the present disclosure includes a new method for pre-packing and post-packing an implant, such as, for example, an expandable cage all at one time with little to no hassle. The method includes using new types of allograft to provide an opportunity for a better delivery method. The cage includes a port of a specific diameter that matches perfectly with the design of a tip of a syringe, funnel, or other delivery device. The cage can be completely filled at one time in both the current pre and post-packing cavities. It would also ensure that the graft is pressed up tight against the endplates, providing a better chance of fusion. This greatly reduces the number of steps the surgeon would perform at the end of the procedure, which would encourage the use of a biologic product that could be pre-loaded or easily loaded into the delivery device on the back table.

In one embodiment, the present system includes a spinal implant including an endcap that aligns a lock for fixation with the spinal implant. In one embodiment, the present system includes an articulating endcap in a corpectomy device and/or vertebral body replacement device configured to align a locking element, such as, for example, a set screw for fixation in a selected orientation. In one embodiment, the alignment of the set screw facilitates locking in situ. In one embodiment, the set screw is oriented perpendicular to or slightly offset from the front of the implant to facilitate locking of the endcap along an approach utilized for implantation. In some embodiments, the spinal implant is expandable.

In one embodiment, the endcap includes a cavity configured to align a set screw such that a tip of the set screw contacts a spherical cut of a post of a spinal implant, which allows for articulation. In some embodiments, the endcap is oriented to an angle relative to a longitudinal axis of the post such that the cavity is configured to orient the set screw at an angle relative to the longitudinal axis. In some embodiments, the angle corresponds to an initial starting position, for example, such that the endcap is positioned perpendicular to the post. In some embodiments, the angulation of the set screw facilitates insertion of the set screw when the endcap is in a fully tilted position. In some embodiments, the angulation of the cavity provides access to the cavity such that the set screw is positioned perpendicular to the post. In some embodiments, angulation of the cavity and tilting of the endcap positions the set screw parallel to the vertebral endplate facilitating access to the set screw.

In one embodiment, the spinal implant comprises a post including a stepped configuration, such as, for example, a wedding cake configuration at a first end. In some embodiments, the stepped configuration provides for smoother articulation. In one embodiment, providing the stepped configuration on a post results in a significant reduction in cost in both manufacturing and inspection. In one embodiment, the step configuration is configured to engage an underside surface of the endcap to facilitate fixation of the endcap with the post.

In one embodiment, the spinal implant includes an anti-back out portion to prevent the set screw from fully backing out. In one embodiment, the cavity of the end cap includes a staked thread configured to prevent back out. In some embodiments, the staked thread allows the set screw to back out sufficiently to unlock the endcap while preventing the endcap from disengaging from the post.

In one embodiment, the spinal implant comprises an endcap including a counter bore within the set screw cavity. In some embodiments, the spinal implant is assembled with a method such that the set screw is assembled from the inside of the post and backed out until it reaches a thread-stop. In some embodiments, the method includes the step of staking for deforming an end of the counter-bore to prevent over advancing the set screw. In some embodiments, when the set screw is in the fully backed out position, the ring and post have clearance to be assembled.

In one embodiment, the spinal implant has torsion slots configured to prevent an instrument, such as, for example, an inserter from being undesirably attached to the spinal implant, for example, upside down. In some embodiments, the spinal implant allows a jaw-like connection with the inserter and provides a rigid engagement.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a spinal implant, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-17, there are illustrated components of a surgical system, such as, for example, a spinal implant system 10 including a spinal implant 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 10 may be employed with surgical procedures, such as, for example, corpectomy and discectomy, which include fusion and/or fixation treatments that employ implants to restore the mechanical support function of vertebrae.

Figure 3:
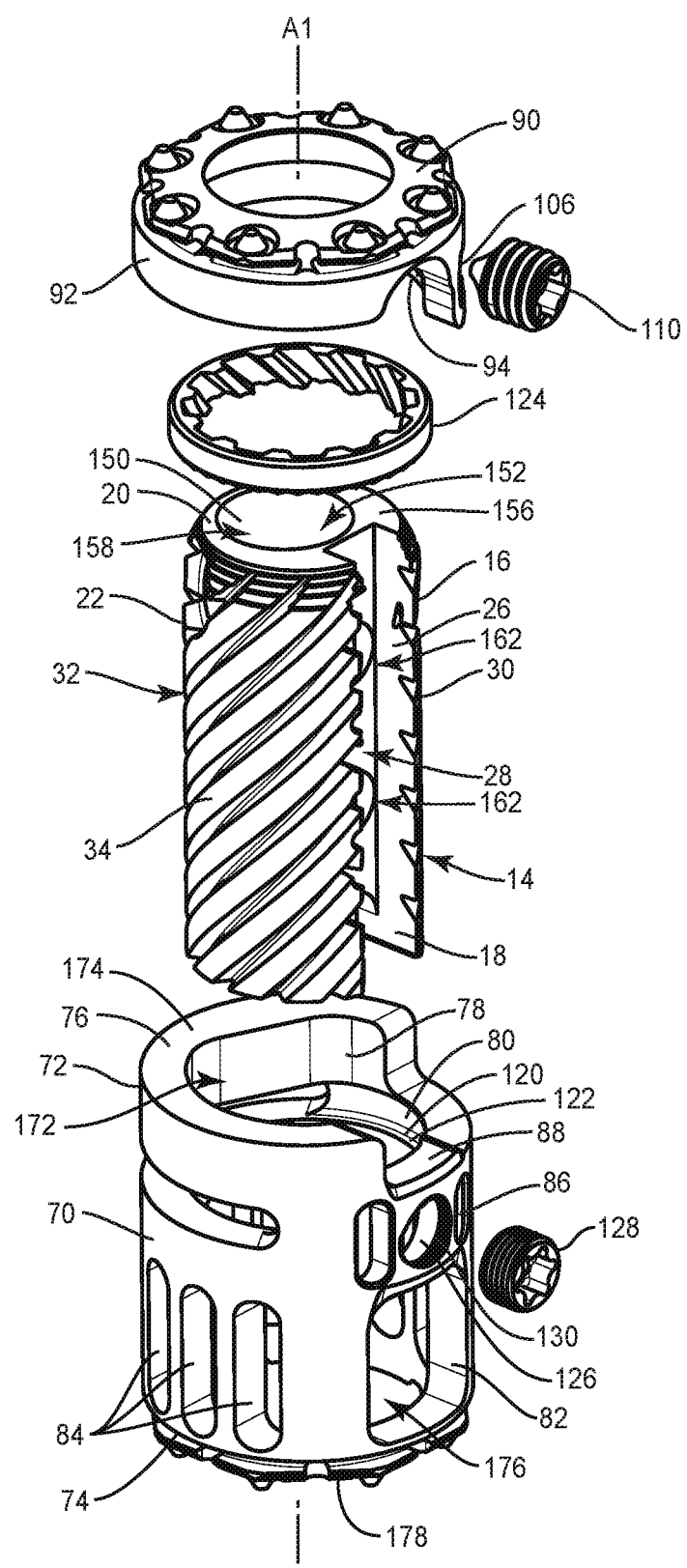
FIG. 3 is a perspective view of the components shown in FIG. 1 with parts separated.
Figure 4:
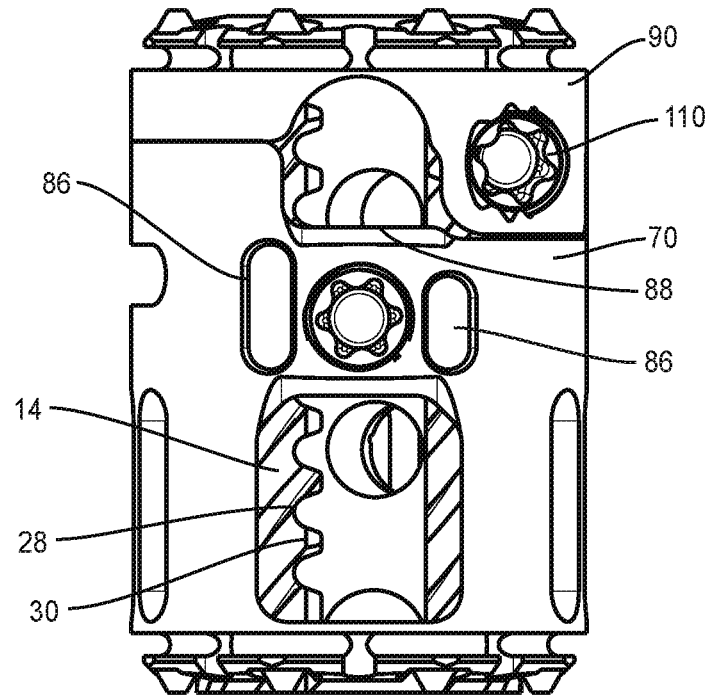
FIG. 4 is a side view of the components shown in FIG. 1.
Figure 5:
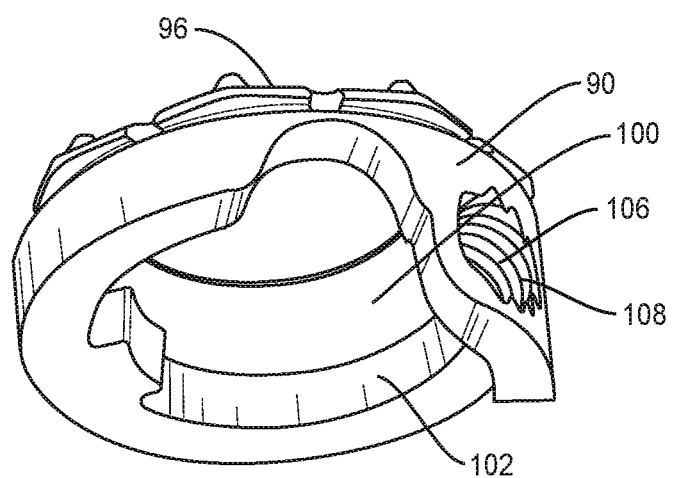
FIG. 5 is a perspective view of a component of the system shown in FIG. 1.
Figure 6:
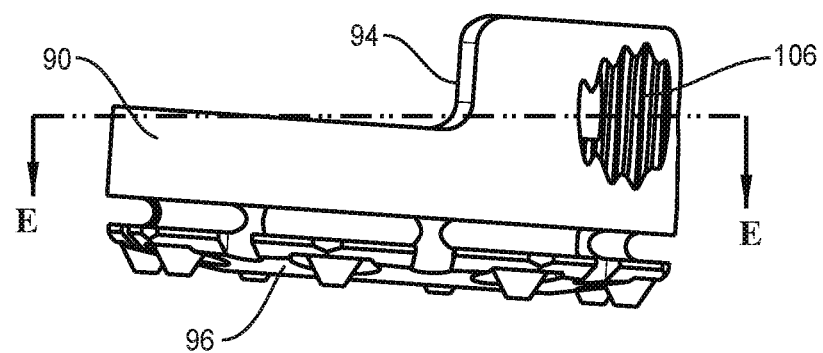
FIG. 6 is a side view of the component shown in FIG. 5.
Figure 7:
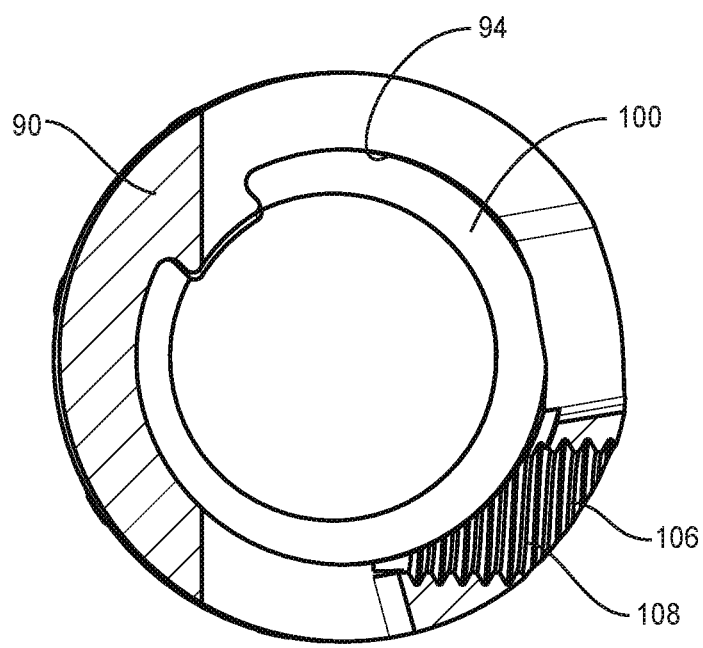
FIG. 7 is a cross section view along the lines E-E shown in FIG. 6.
Figure 8:
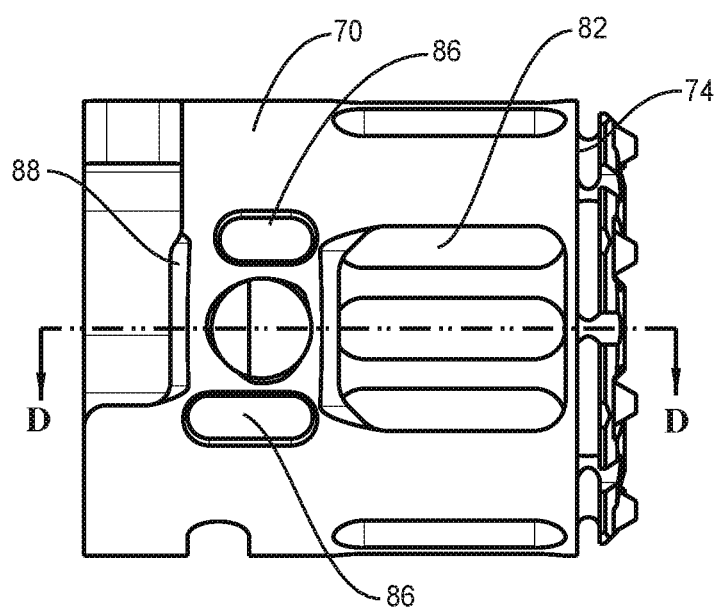
FIG. 8 is a side view of components of the system shown in FIG. 1.
Figure 9:
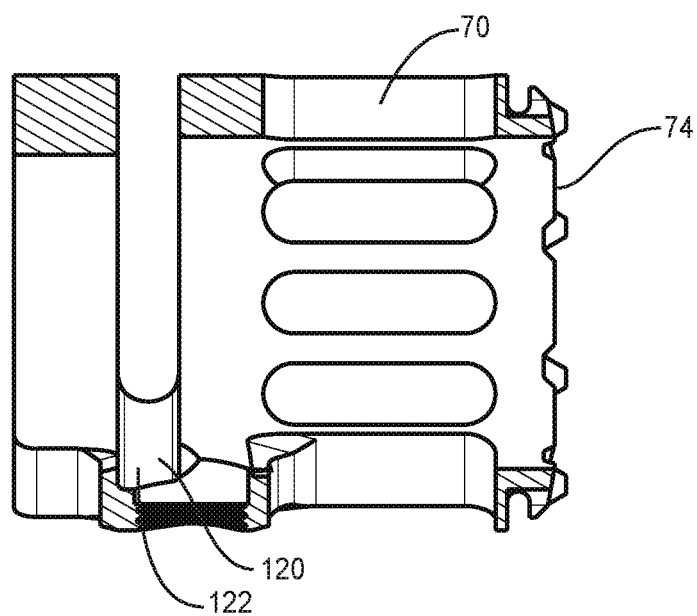
FIG. 9 is a cross section view along the lines D-D shown in FIG. 8.

Spinal implant system 10 includes a vertebral body replacement implant 12 including a member, such as, for example, an inner body 14. Body 14 has a tubular configuration and is oriented for disposal within an axial channel, such as, for example, an axial cavity 80, as described herein. Body 14 defines a longitudinal axis A1. Body 14 extends between an end 16 and an end 18, as shown in FIG. 3. Body 14 includes a wall, such as, for example, a tubular wall 20. In some embodiments, wall 20 has a cylindrical cross-section and an outer surface 22. In some embodiments, the cross-sectional geometry of wall 20 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, outer surface 22 may be smooth, even, rough, textured, porous, semi-porous, dimpled and/or polished.

Wall 20 includes an axial opening, such as, for example, an axial slot 26. Slot 26 has a substantially rectangular configuration to facilitate axial translation of body 14 relative to a member, such as, for example, an outer body 70, as described herein. In some embodiments, slot 26 may have various configurations, such as, for example, arcuate, oval, oblong, triangular, polygonal having planar or arcuate side portions, irregular, uniform or non-uniform. Slot 26 includes a gear rack 28 having a plurality of teeth 30 that are disposed therealong. Teeth 30 are engageable with a surgical instrument to facilitate expansion and/or contraction of implant 12, as described herein. For example, in some embodiments, the expansion mechanism for spinal implant 12 may comprise that which is disclosed in U.S. patent application Ser. No. 13/650,883, published as US 2014-0107787 A1, which is hereby incorporated by reference in its entirety.

A portion of outer surface 22 comprises a helical gear 32 having a plurality of teeth 34 engageable with a band 124 to facilitate locking the height of implant 12. Teeth 34 are spaced apart in a helical configuration and disposed at an angular orientation relative to axis A1 such that band 124 is translatable in a helical gear configuration about surface 22. In some embodiments, the components of implant 12 may translate to expand and/or contract implant 12 via engagement of the bodies without a band configuration. For example, in some such embodiments, band 124 may comprise a locking ring configured to rotate about surface 22 as a separate instrument is engaged with slot 26, which includes a gear rack 28 having a plurality of teeth 30 that are disposed therealong. Teeth 30 are engageable with a surgical instrument to facilitate expansion and/or contraction of implant 12 until a user locks the height of implant 12, using setscrew 128, which is provided to fix body 14 relative to body 70 by locking the helical position of band 124 along surface 22.

Figure 10:
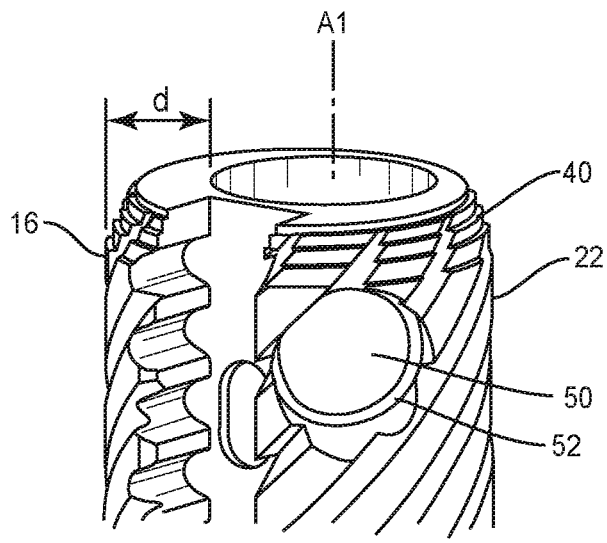
FIG. 10 is a break away view of components of the system shown in FIG. 1.
Figure 11:
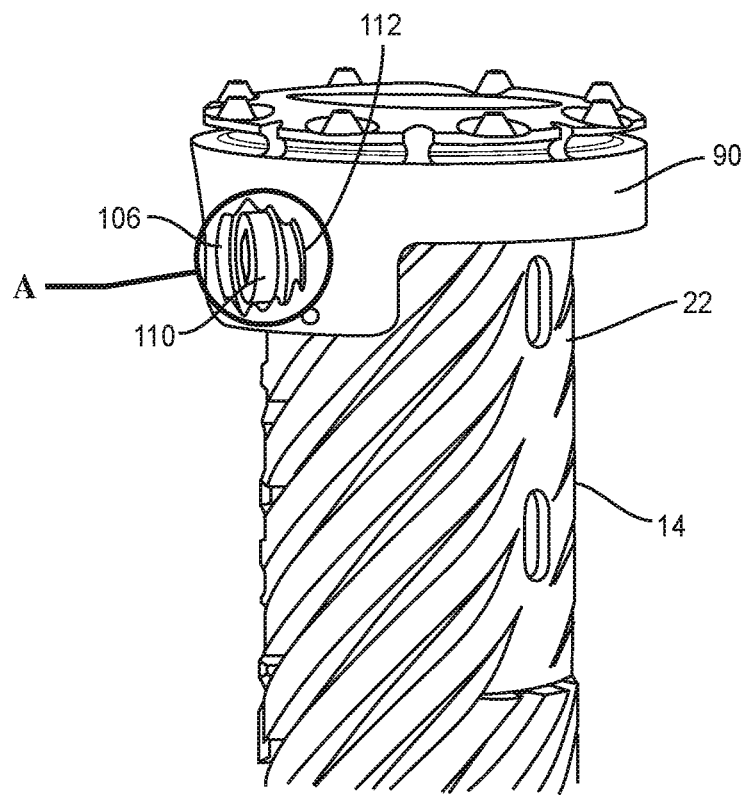
FIG. 11 is a perspective view of components of the system shown in FIG. 1.

In some embodiments, a portion of outer surface 22 at end 16 includes a decreasing dimension d or taper, as shown in FIG. 10. End 16 includes a plurality of steps 40 disposed along axis A1. Steps 40 are configured for engagement with a member, such as, for example, a cap 90 to provide selective positioning of cap 90 and to facilitate rotation of cap 90 relative to axis A1 and body 14. In some embodiments, end 16 includes one or a plurality of steps 40. In some embodiments, end 16 can include a surface that may be smooth, rough, textured, porous, semi-porous, dimpled and/or polished to facilitate engagement with cap 90.

Figure 17:
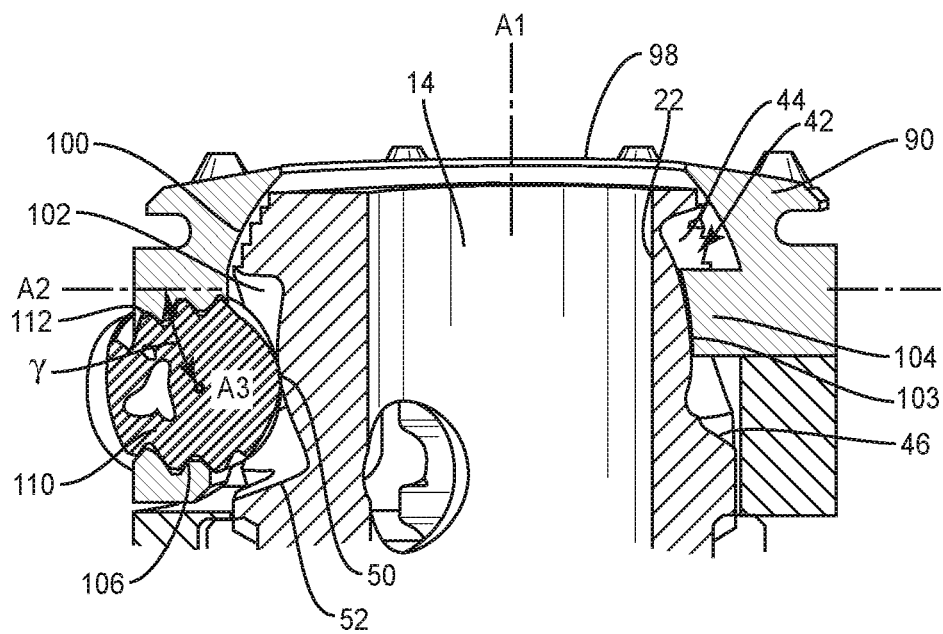
FIG. 17 is a break away view of components of the system shown in FIG. 1.

Surface 22 includes a wall 44 and a wall 46 that define a cavity 42, as shown in FIG. 17. Walls 44, 46 define movable limits of a flange 104 of cap 90. Flange 104 is rotatable relative to axis A1 and body 14 between a first angular limit provided by wall 44 and a second angular limit provided by wall 46, as described herein. Cap 90 is rotatable relative to axis A1 and body 14 between the movable limits to facilitate positioning of implant 12 for delivery and/or with tissue, and access to implant 12 for surgical instrument engagement and locking, as well as avoiding disassembly of the components of implant 12 during insertion with tissue. In one embodiment, the moveable limit includes a plurality of limits, each limit corresponding to one of a plurality of orientations of cap 90 relative to body 14.

Surface 22 includes an engagement surface, such as, for example, spherical surface 50. In some embodiments, surface 50 is recessed from surface 22 within a circumferential wall 52. In some embodiments, surface 50 is flush with surface 22. In some embodiments, surface 50 is raised from surface 22. Surface 50 is configured for engagement with a locking element, such as, for example, a set screw 110 to fix cap 90 relative to body 14 in a selected orientation, as described herein.

Figure 19:
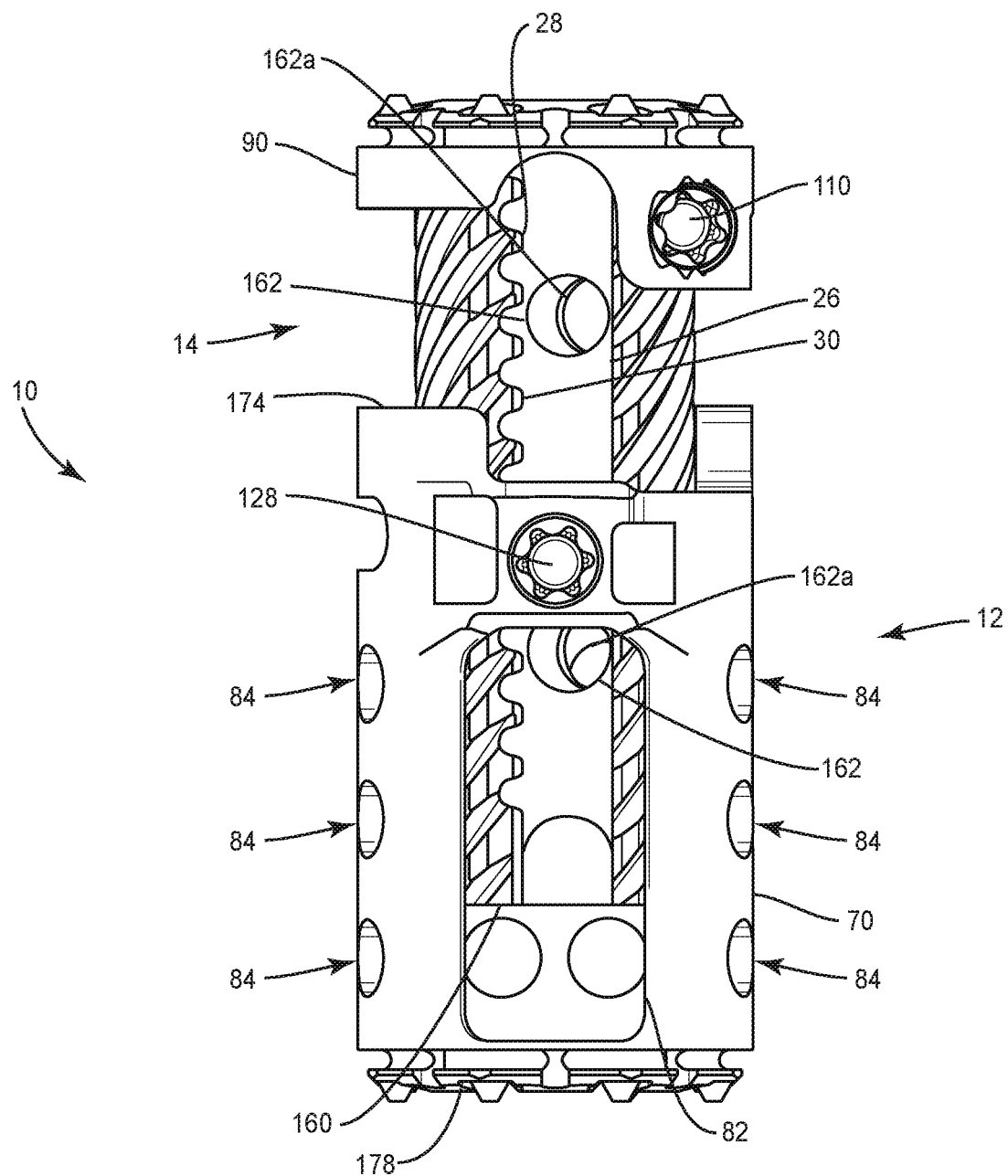
FIG. 19 is a side view of components of the system shown in FIG. 1.
Figure 21:
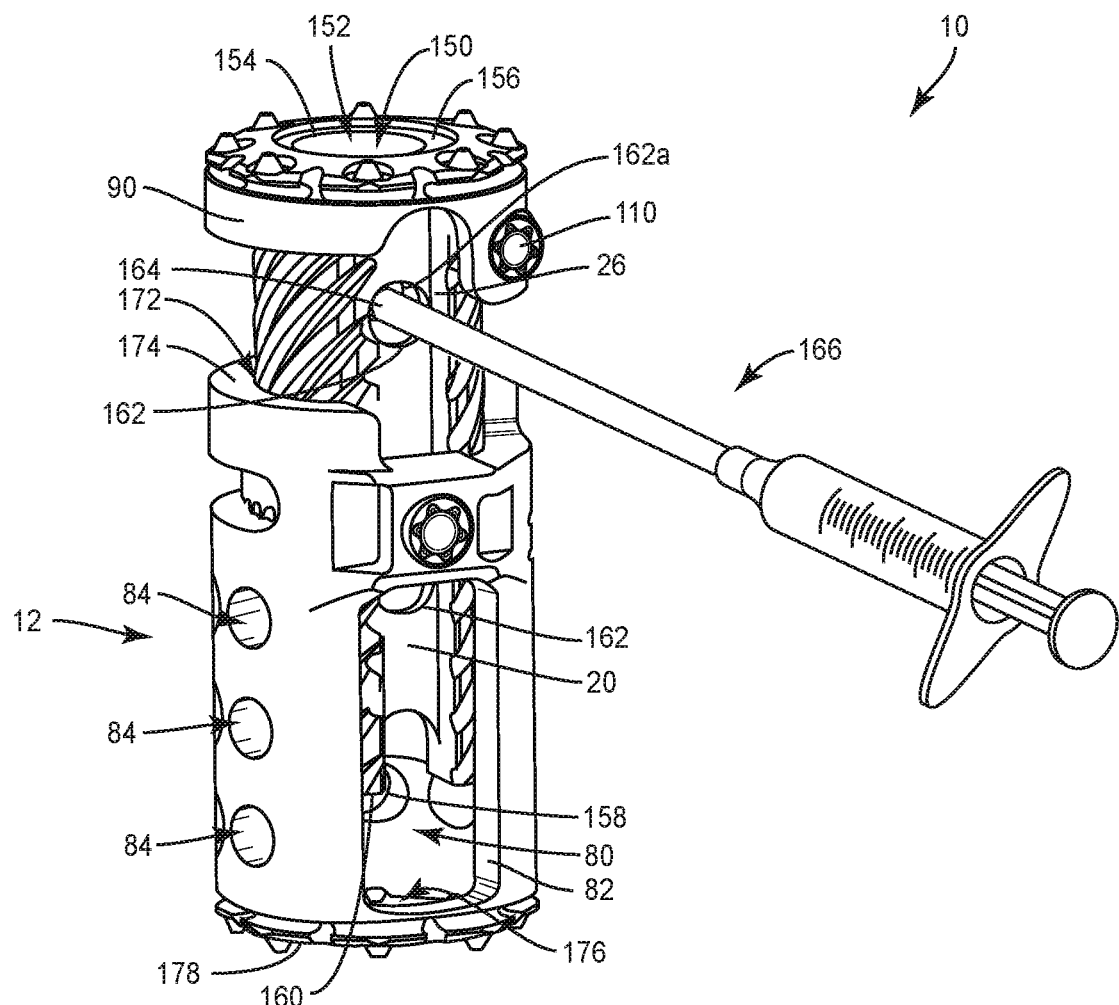
FIG. 21 is a perspective view of components of one embodiment of a surgical system in accordance with the principles of the present disclosure disposed with vertebrae.

In some embodiments, body 14 includes an inner surface 150 opposite surface 22. Surface 150 defines an axial passageway 152 that is coaxial with axis A1, as shown in FIGS. 3 and 21, for example. Body 14 includes an opening 154 that extends through an end surface 156 of body 14 and an opening 158 that extends through an opposite end surface 160 of body. Openings 154, 158 are in communication with passageway 152. Passageway 152 is spaced apart from slot 26 by wall 20. Wall 20 includes one or a plurality of ports, such as, for example, one or a plurality of openings 162 that extend through a thickness of wall 20. Openings 162 are each in communication with slot 26 and passageway 152. In some embodiments, body 14 includes one or a plurality of ports, such as, for example, openings 162a that are each in communication with passageway 152. In some embodiments, at least one of openings 162a is aligned and/or coaxial with one of openings 162, as shown in FIGS. 19 and 21, for example. In some embodiments, passageway 152 may be disposed at alternate orientations, relative to axis A1, such as, for example, transverse, perpendicular and/or other angular orientations such as acute or obtuse, co-axial and/or may be offset or staggered. In some embodiments, openings 162a may be disposed at alternate orientations, relative to one of openings 162, such as, for example, transverse, perpendicular and/or other angular orientations such as acute or obtuse, co-axial and/or may be offset or staggered.

In some embodiments, openings 162, 162a are configured for disposal of a tip 164 of a delivery instrument, such as, for example, a funnel or a syringe 166 (FIG. 21) to deliver bone graft into passageway 152, as discussed herein. In some embodiments, openings 162, 162a have a specific size and/or shape that matches the size or shape of tip 164. For example, when tip 164 has a circular cross-sectional configuration, openings 162, 162a can have a circular cross-sectional configuration with a diameter of tip 164 being slightly less than diameters of openings 162, 162a to allow tip 164 to be positioned in openings 162, 162a. Likewise, when tip 164 has a polygonal cross-sectional configuration, openings 162, 162a can have a polygonal cross-sectional configuration with a diameter of tip 164 being slightly less than diameters of openings 162, 162a to allow tip 164 to be positioned in openings 162, 162a. In some embodiments, an outer surface of tip 164 directly engages surfaces that define openings 162, 162a when tip 164 is inserted into openings 162, 162a such that tip 164 forms a friction or interference fit with body 14. In some embodiments, the outer surface of tip 164 is spaced apart from surfaces that define openings 162, 162a when tip 164 is inserted into openings 162, 162a. In some embodiments, openings 162, 162a and tip 164 can have various shape configurations, such as, for example, oval, oblong, polygonal, irregular, uniform, non-uniform, variable and/or tapered.

Cap 90 includes an outer surface 92 and an inner surface 94. Surface 92 is configured for engagement with tissue. Surface 92 includes a surface 96, which includes planar and dimpled portions for engagement with tissue, and defines an axis A2 oriented transverse to axis A1, as shown in FIGS. 14-17. In some embodiments, surface 96 and/or axis A2 may be disposed in transverse orientations relative to axis A1, such as, for example, perpendicular and/or other angular orientations such as acute or obtuse, and/or may be offset or staggered. In some embodiments, surface 96 can include a surface that may be rough, textured, porous, semi-porous, dimpled and/or polished to facilitate engagement with tissue. In some embodiments, surface 96 can include one or more openings to deliver an agent, such as, for example, bone graft to a vertebra endplate.

Surface 94 includes a substantially planar surface 98, an angled surface 100 and annular surfaces 102, 103, a shown in FIG. 17. Angled surface 100 is disposed circumferentially about cap 90. Surfaces 98, 100, 102, 103 are configured for engagement with steps 40 and/or surface 22 to facilitate rotation of cap 90 relative to axis A1 and body 14, as described herein. Apices of annular surfaces 102, 103 may be offset at an angle (ranging from 0 to 20 degrees) relative to axis A2, as shown generally in FIG. 17, to allow for a larger freedom of motion for cap 90.

Figure 14:
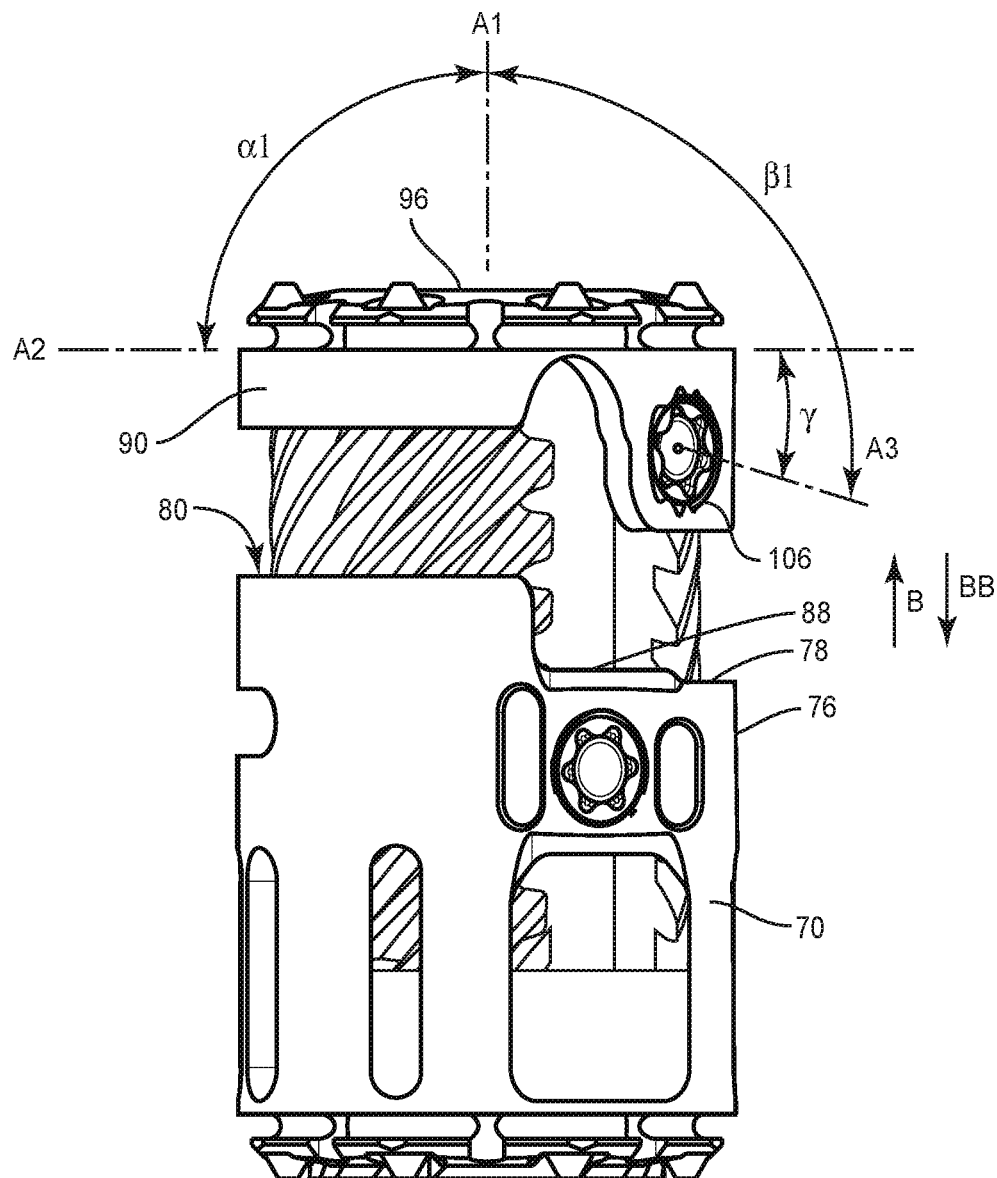
FIG. 14 is a side view of components of the system shown in FIG. 1.
Figure 15:
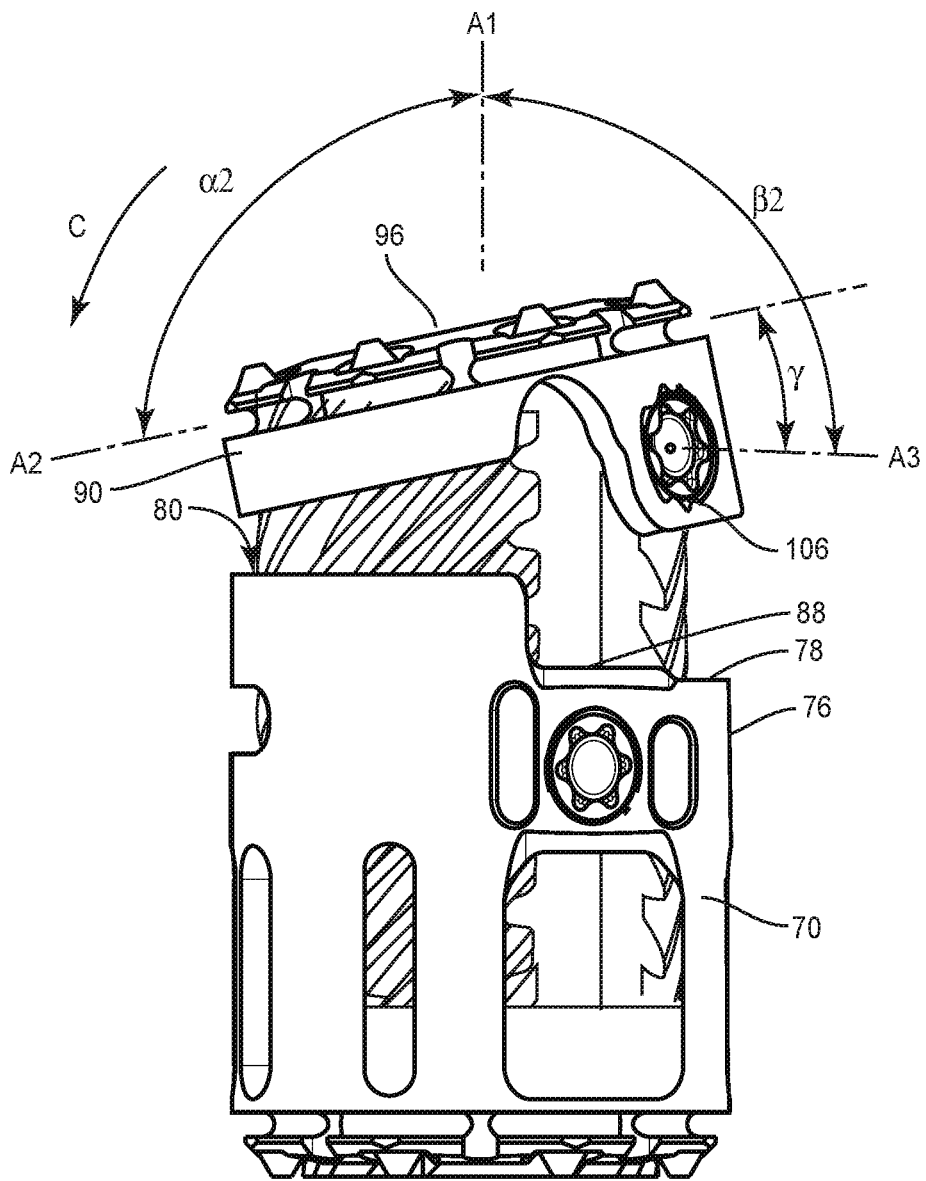
FIG. 15 is a side view of components of the system shown in FIG. 1.

Cap 90 is rotatable about body 14 such that surface 96 and/or axis A2 may be disposed in one or a plurality of transverse orientations and at one or a plurality of angular orientations a relative to axis A1, as shown in FIGS. 14-17. In some embodiments, surface 96 and/or axis A2 are moveable relative to axis A1 between a first orientation such that surface 96 and/or axis A2 of cap 90 is disposed at an angle α1 relative to axis A1, as shown in FIG. 14, and a second orientation such that surface 96 and/or axis A2 of cap 90 is disposed at a selected angle α2 relative to axis A1, as shown in FIG. 15.

In some embodiments, angle α1 is 90 degrees. In some embodiments, surface 96 and/or axis A2 are moveable relative to axis A1 through an angular range of +/−45 degrees. In some embodiments, in a first orientation, angle α1 is substantially 90 degrees and surface 96 and/or axis A2 are moveable relative to axis A1 to a second orientation such that angle α2 equals angle α1 plus an angle within an angular range of +/−25 degrees. In some embodiments, cap 90 is moveable relative to axis A1 in one or more planes of a body, such as, for example, vertical, horizontal, diagonal, bi-lateral, transverse, coronal and/or sagittal planes of a body.

Figure 16:
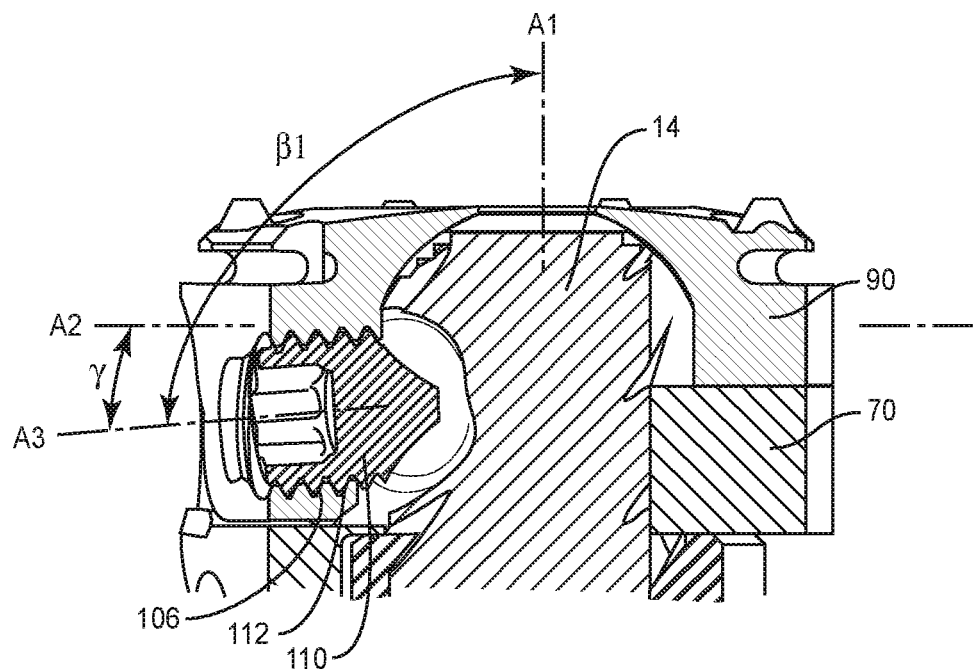
FIG. 16 is a break away view of components of the system shown in FIG. 1.

Cap 90 includes flange 104 configured for movable disposal with cavity 42 and engagement with walls 44, 46. Flange 104 extends from surface 94 and is oriented towards body 14, as shown in FIG. 17. Cap 90 includes a cavity 106 that defines an axis A3 disposed transverse to axes A1, A2, as shown in FIGS. 14-16. Axis A3 is offset from axis A1 in a selected plane, as shown in FIG. 17.

Cavity 106 is configured to orient set screw 110 transverse, such as, for example, perpendicular and/or offset from axis A1 upon rotation of cap 90 to facilitate engagement of set screw 110 with surface 50. In some embodiments, cavity 106 orients set screw 110 for engagement with surface 50 to lock cap 90 with body 14 along the same surgical passageway utilized to insert implant 12 with tissue, as described herein.

Axis A3 is disposed at a fixed orientation at an angle γ relative to axis A2. In some embodiments, axis A3 is disposed at an angle γ of 4 degrees relative to axis A2. In some embodiments, axis A3 is moveable relative to axis A1 between a first orientation such that axis A3 is disposed at an angle β1 relative to axis A1, as shown in FIGS. 14 and 16, and a second orientation such that axis A3 is disposed at a selected angle β2 relative to axis A1, as shown in FIG. 15. In the second orientation, β2 approaches substantially 90 degrees and/or a perpendicular orientation of axis A3 relative to axis A1 to facilitate engagement of set screw 110 with surface 50. In some embodiments, axis A3 is moveable relative to axis A1 in one or more planes of a body, such as, for example, vertical, horizontal, diagonal, bi-lateral, transverse, coronal and/or sagittal planes of a body.

Figure 12:
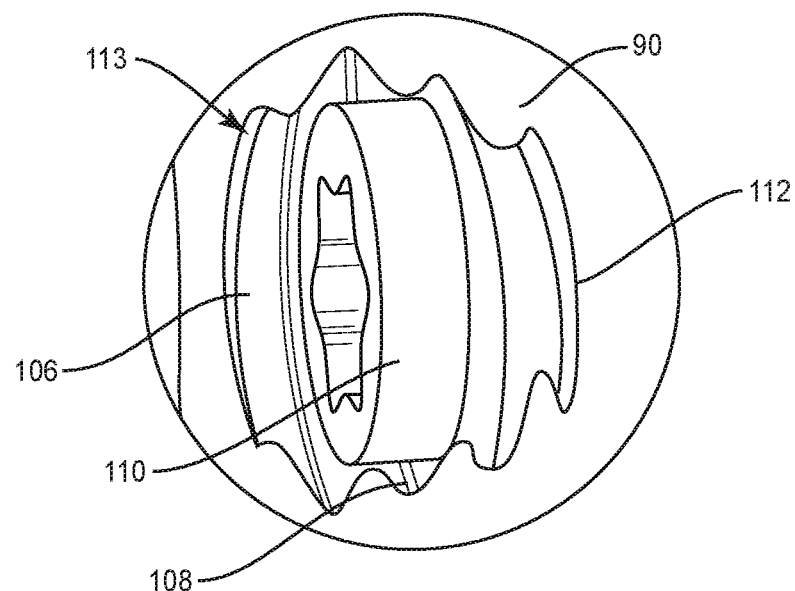
FIG. 12 is an enlarged view of detail A shown in FIG. 11.
Figure 13:
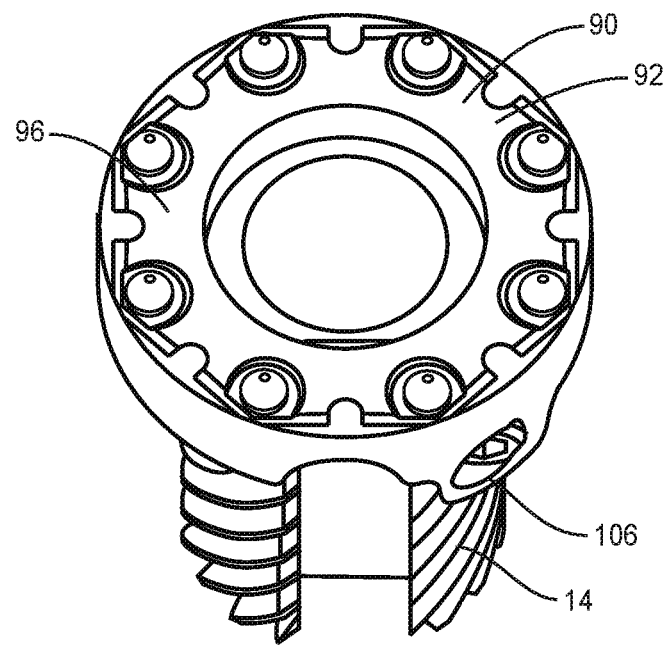
FIG. 13 is a perspective view of components of the system shown in FIG. 1.

Cavity 106 includes a threaded surface 108 configured for engagement with set screw 110. In one embodiment, as shown in FIG. 12, cavity 106 includes an end thread 112. Thread 112 prevents set screw 110 from fully backing out of cap 90, as described herein. In one embodiment, setscrew 110 is threaded into cavity 106 until set screw 110 approaches thread 112. For example, thread 112 may be staked such that proximal end 113 of thread 112 is deformed to prevent set screw 110 from fully backing out of cap 90. Set screw 110 is positioned in cavity 106 to fix cap 90 relative to body 14 in a selected orientation, as described herein.

Body 70 includes a tubular configuration. Body 70 extends between an end 72 and an end 74. Body 70 extends in a linear configuration. In some embodiments, body 70 may extend in alternate configurations, such as, for example, arcuate, offset, staggered and/or angled portions, which may include acute, perpendicular and obtuse. End 74 includes a surface that defines planar and dimpled portions for engagement with tissue. In some embodiments, end 74 can include a surface that may be rough, textured, porous, semi-porous, dimpled and/or polished such that it facilitates engagement with tissue. In some embodiments, the tissue comprises vertebral tissue, which may include intervertebral tissue, endplate surfaces, cancellous bone and/or cortical bone.

Body 70 includes a wall, such as, for example, a tubular wall 76. Wall 76 includes an inner surface 78 that defines an axial cavity 80 extending between ends 72, 74. Body 14 is configured for disposal with cavity 80. In some embodiments, wall 76 has a cylindrical cross-section. In some embodiments, the cross-section geometry of wall 76 may include, such as, for example, round, oval, oblong, triangular, polygonal having planar or arcuate side portions, irregular, uniform, non-uniform, consistent, variable, horseshoe shape, U-shape or kidney bean shape. In some embodiments, surface 78 is smooth or even. In some embodiments, surface 78 may be rough, textured, porous, semi-porous, dimpled and/or polished. In some embodiments, body 70 includes an opening 172 that extends through an end surface 174 of body 70 and an opening 176 that extends through an opposite end surface 178 of body 70. Openings 172, 176 are in communication with cavity 70.

Wall 76 defines a port, such as, for example, lateral opening 82 that is in communication with cavity 80. In some embodiments, opening 82 is configured for disposal of an instrument, such as, for example, an inserter utilized to facilitate expansion of body 14 relative to body 70, as described herein. For example, opening 82 may be configured to receive a separate pinion instrument (not shown) adapted to engage gear rack 28. The inserter instrument may, in some embodiments, comprise instruments disclosed in U.S. patent application Ser. No. 14/450,038, which is hereby incorporated by reference in its entirety.

In some embodiments, wall 76 defines openings 82, 84 configured to receive an agent, which may include bone graft (not shown) and/or other materials, as described herein, for employment in a fixation or fusion treatment used for example, in connection with a corpectomy. In one embodiment, the agent may include therapeutic polynucleotides or polypeptides and bone growth promoting material, which can be packed, coated or otherwise disposed on or about the surfaces of the components of system 10, including implant 12. The agent may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of implant 12 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines. In some embodiments, openings 82, 84 can have various shape configurations, such as, for example, oval, oblong, polygonal, irregular, uniform, non-uniform, variable and/or tapered. In some embodiments, openings 84 are arranged in a row, with openings 84 each having an oblong shape or configuration, as shown in FIG. 3, for example. In some embodiments, openings 84 are arranged in a column, with openings 84 each having a circular shape or configuration, as shown in FIG. 21, for example.

In some embodiments, opening 82 is configured for disposal of a tip 168 of a delivery instrument, such as, for example, a funnel or a syringe 170 (FIG. 21) to deliver bone graft into cavity 80, as discussed herein. In some embodiments, opening 82 has a specific size and/or shape that matches the size or shape of tip 168. For example, when tip 168 has a circular cross-sectional configuration, opening 82 can have a circular cross-sectional configuration with a diameter of tip 168 being slightly less than a diameter of opening 82 to allow tip 168 to be positioned in opening 82. Likewise, when tip 168 has a polygonal cross-sectional configuration, opening 82 can have a polygonal cross-sectional configuration with a diameter of tip 168 being slightly less than diameters of opening 82 to allow tip 168 to be positioned in opening 82. In some embodiments, an outer surface of tip 168 directly engages surfaces that define opening 82 when tip 168 is inserted into opening 82 such that tip 168 forms a friction or interference fit with body 70. In some embodiments, the outer surface of tip 168 is spaced apart from surfaces that define opening 82 when tip 168 is inserted into opening 82. In some embodiments, opening 82 and tip 168 can have various shape configurations, such as, for example, oval, oblong, polygonal, irregular, uniform, non-uniform, variable and/or tapered. In some embodiments, the tip of the syringe and mating hole on the implant form a ball and socket type connection to allow the syringe to engage with the hole in an off-axis orientation, increasing the ease of inserting graft through the hole In one embodiment, wall 76 includes cavities, such as, for example, slots 86 configured for attachment with a surgical inserter to prevent the inserter from being incorrectly attached, such as, for example, upside down. Wall 76 includes a cut out 88 configured to facilitate engagement with the inserter. Cutout 88 facilitates engagement of the inserter with body 70 by providing a rigid connection between the inserter and body 70.

Surface 78 includes a portion 120, as shown in FIG. 3, which defines a circumferential cavity 122 disposed adjacent end 72. Portion 120 has a substantially smooth or even surface configuration such that cavity 122 is configured for disposal of band 124. Band 124 is slidably movable within cavity 122 for rotation relative to portion 120. In some embodiments, portion 120 may be rough, textured, porous, semi-porous, dimpled and/or polished.

In one embodiment, body 70 includes a counter-bore 126. In one embodiment, a setscrew 128 is provided to fix body 14 relative to body 70. Set screw 128 includes a thread stop 130, as shown in FIG. 3. Set screw 128 is assembled from the inside of body 70 and backed out until set screw 128 approaches thread stop 130. Counter-bore 126 is staked to deform an end of counter-bore 126 to prevent over advancing of setscrew 128 and facilitate assembly of body 14 and cap 90 with body 70.

In operation, implant 12 is disposed in a first orientation, as shown in FIG. 1, such that body 14 and body 70 are disposed in a telescopic arrangement for delivery and implantation adjacent a surgical site. Bodies 14, 70 are seated such that substantially all of inner body 14 is disposed within outer body 70 in a nested configuration. Cap 90 is flush with end 16 such that axis A2 is substantially perpendicular to axis A1 and cavity 106 is disposed such that axis A3 is disposed transverse to axes A1, A2 and offset from axis A1. In the first orientation, a surgical inserter, which may comprise a rotatable pinion, is disposed within opening 82, slots 86 and cutout 88 and engaged with gear rack 28 and actuated and/or rotated such that the inserter engages gear rack 28 for axial translation of body 14 relative to body 70. Rotation of the inserter causes axial translation of body 14 relative to body 70 to expand implant 12. In some embodiments, the inserter is rotated in the opposite direction to drive body 14 in a second axial direction and cause axial translation of body 14 relative to body 70 to contract and/or collapse implant 10 from an expanded configuration.

Figure 18:
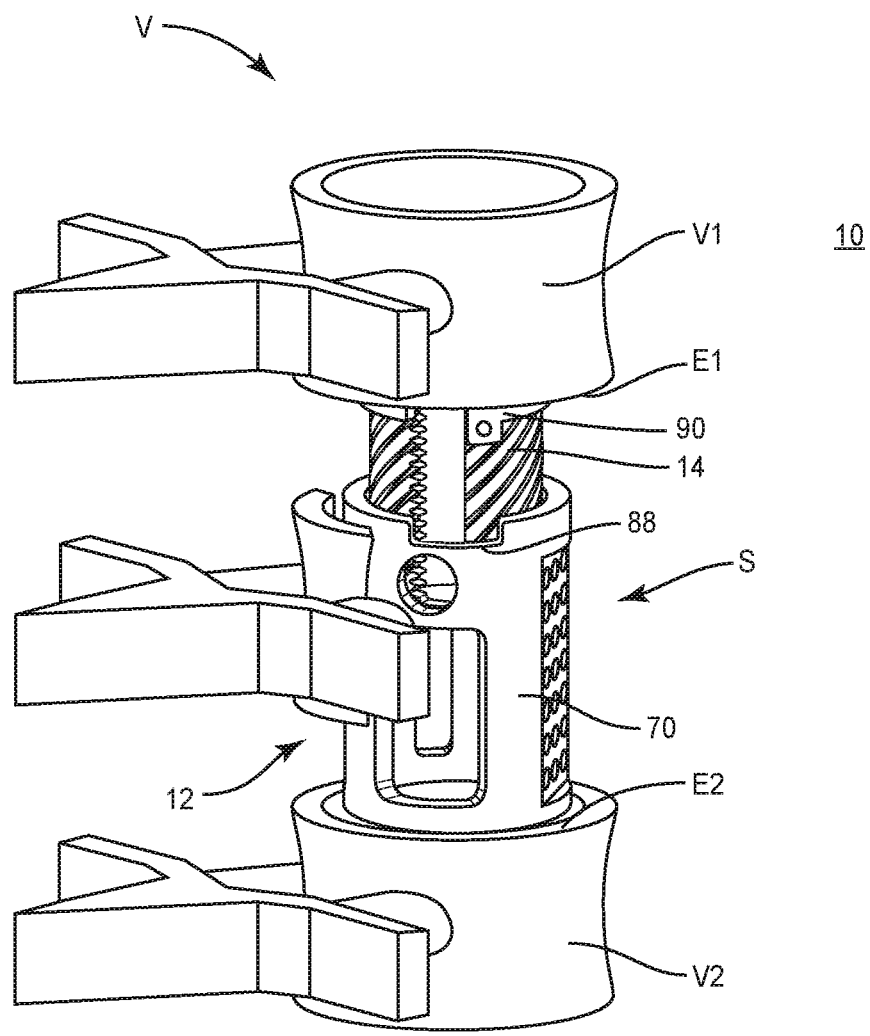
FIG. 18 is a perspective view of components of one embodiment of a surgical system in accordance with the principles of the present disclosure disposed with vertebrae.

In some embodiments, in a second, expanded orientation, as shown in FIG. 18 for example, cap 90 and end 74 are disposed to engage adjacent vertebral soft tissue and bone surfaces, as will be described, to restore height and provide support in place of removed vertebrae and/or intervertebral tissue. In one embodiment, implant 12 is expanded to a second orientation at a selected amount of spacing and/or distraction between vertebrae such that cap 90 engages a first vertebral surface and end 74 engages a second vertebral surface to restore vertebral spacing and provide distraction and/or restore mechanical support function. In one embodiment, implant 12 is expanded, as discussed herein, progressively and/or gradually to provide an implant configured to adapt to the growth of a patient including the vertebrae. In some embodiments, the height of implant 12 may also be decreased over a period of time and/or several procedures to adapt to various conditions of a patient.

In some embodiments, as body 14 expands, as described herein, cap 90 rotates relative to axis A1 between a first orientation such that surface 96 and/or axis A2 of cap 90 are disposed at angle $\alpha 1$ relative to axis A1, as shown in FIG. 14, and a second orientation such that surface 96 and/or axis A2 of cap 90 are disposed at selected angle $\alpha 2$ relative to axis A1, as shown in FIG. 15. Rotation of cap 90 allows surface 96 to adjust to an angle to accommodate a specific angle of vertebral tissue, with tissue and/or a treatment. As cap 90 rotates, surfaces 100, 102 translate about end 16 to accommodate the angle changes of surface 96. Walls 44, 46 provide a range of motion limit and resist and/or prevent cap 90 from rotating about axis A1 beyond a selected limitation of movement of cap 90. The intersection between surfaces 100, 102 contacts steps 40 to limit rotation of cap 90.

Axis A3 maintains a fixed orientation at an angle $\gamma$ relative to axis A2 during rotation of cap 90. As cap 90 rotates, axis A3 is moveable relative to axis A1 between a first orientation such that axis A3 is disposed at an angle $\beta 1$ relative to axis A1, as shown in FIGS. 14 and 16, and a second orientation such that axis A3 is disposed at a selected angle 12 relative to axis A1, as shown in FIG. 15. In the second orientation, angle $\beta 2$ approaches substantially 90 degrees and/or a perpendicular orientation of axis A3 relative to axis A1 to facilitate engagement of set screw 110 with surface 50 to fix cap 90 in a selected orientation relative to body 14 and/or body 70.

In some embodiments, implant 12 provides a footprint that improves stability and decreases the risk of subsidence into tissue. In some embodiments, implant 12 provides height restoration between vertebral bodies, decompression, restoration of sagittal and/or coronal balance and/or resistance of subsidence into vertebral endplates.

Referring to FIG. 18, in assembly, operation and use, spinal implant system 10 including implant 12, similar to the systems and methods described with regard to FIGS. 1-17, is employed with a surgical procedure, such as, for example, a lumbar corpectomy for treatment of a spine of a patient including vertebrae V. Spinal implant system 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of implant 12 with vertebrae V.

Spinal implant system 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes a vertebra V1 and a vertebra V2. A diseased and/or damaged vertebra and intervertebral discs are disposed between vertebrae V1, V2. In some embodiments, spinal implant system 10 is configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, which may include diseased and/or damaged intervertebral discs, are removed to create a vertebral space S.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. Implant 12 is provided with at least one agent, similar to those described herein, to promote new bone growth and fusion to treat the affected section of vertebrae V.

Set screw 110 is engaged with cavity 106 from surface 94 of cap 90 and threaded into cavity 106 until set screw 110 approaches thread 112, as described herein. Bodies 14, 70 are seated such that substantially all of inner body 14 is disposed within outer body 70 in a nested configuration and cap 90 is flush with end 16 and axis A2 is disposed perpendicular to axis A1. The inserter is engaged with opening 82, slots 86 and cutout 88. Implant 12 is delivered to the surgical site adjacent vertebrae V along the surgical passageway. The inserter delivers implant 12 into prepared vertebral space S, between vertebrae V1, V2. Implant 12 is manipulated such that end 74 engages endplate surface E2. A gripping surface of end 74 penetrates and fixes with endplate surface E2. Implant 12 is positioned in a first orientation, as described herein, with endplate surface E2.

Rotation of the inserter causes axial translation of body 14 relative to body 70 to expand implant 12, in a direction shown by arrow B in FIG. 14. In one embodiment, the inserter is rotated in an opposite direction to drive body 14 in a second axial direction, as shown by arrow BB in FIG. 14, and cause axial translation of body 14 relative to body 70 to contract and/or collapse implant 10 from the expanded configuration.

As the inserter is rotated, implant 12 expands to the second orientation, as shown in FIG. 18. As such, implant 12 expands within vertebral space S and surface 96 engages endplate surface E1. Cap 90 rotates relative to axis A1, in the direction shown by arrow C in FIG. 15, from the first orientation, such that surface 96 and/or axis A2 of cap 90 are disposed at angle $\alpha 1$ relative to axis A1, as shown in FIG. 14, to the second orientation such that surface 96 and/or axis A2 of cap 90 are disposed at a selected angle $\alpha 2$ relative to axis A1, as shown in FIG. 15.

Rotation of cap 90 allows surface 96 to adjust to an angle to accommodate a specific angle of endplate surface E1. As cap 90 rotates, axis A3 rotates from angle $\beta 1$ relative to axis A1, as shown in FIGS. 14 and 16, to the second orientation such that axis A3 is disposed at the selected angle $\beta 2$ relative to axis A1, as shown in FIG. 15. In the second orientation $\beta 2$ approaches the substantially perpendicular orientation relative to axis A1 to facilitate access along the surgical pathway to set screw 110 and engagement of set screw 110 with surface 50. Set screw 110 is engaged with surface 50 to lock cap 90 relative to body 14 in a selected orientation, for example, such that surface 96 and/or axis A2 are disposed at a selected angle $\alpha 2$ relative to axis A1 and axis A3 is disposed at the selected angle $\beta 2$ relative to axis A1.

Implant 12 engages and spaces apart opposing endplate surfaces E1, E2 and is secured within vertebral space S to stabilize and immobilize portions of vertebrae V in connection with bone growth for fusion and fixation of vertebrae V1, V2. Fixation of implant 12 with endplate surfaces E1, E2 may be facilitated by the resistance provided by the joint space and/or engagement with endplate surfaces E1, E2.

In some embodiments, implant 12 may engage only one endplate. In some embodiments, one or more agents, as described herein, may be applied to areas of the surgical site to promote bone growth. Components of system 10 including implant 12 can be delivered or implanted as a pre-assembled device or can be assembled in situ. Components of system 10 including implant 12 may be completely or partially revised, removed or replaced in situ. In some embodiments, one or all of the components of system 10 can be delivered to the surgical site via mechanical manipulation and/or a free hand technique.

In one embodiment, implant 12 may include fastening elements, which may include locking structure, configured for fixation with vertebrae V1, V2 to secure joint surfaces and provide complementary stabilization and immobilization to a vertebral region. In some embodiments, locking structure may include fastening elements such as, for example, rods, plates, clips, hooks, adhesives and/or flanges. In some embodiments, system 10 can be used with screws to enhance fixation. In some embodiments, system 10 and any screws and attachments may be coated with an agent, similar to those described herein, for enhanced bony fixation to a treated area. The components of system 10 can be made of radiolucent materials such as polymers. Radiomarkers may be included for identification under x-ray, fluoroscopy, CT or other imaging techniques.

In one embodiment, system 10 includes a plurality of implants 12. In some embodiments, employing a plurality of implants 12 can optimize the amount vertebral space S can be spaced apart such that the joint spacing dimension can be preselected. The plurality of implants 12 can be oriented in a side by side engagement, spaced apart and/or staggered.

In some embodiments, the use of microsurgical and image guided technologies may be employed to access, view and repair spinal deterioration or damage, with the aid of system 10. Upon completion of the procedure, the non-implanted components, surgical instruments and assemblies of system 10 are removed and the incision is closed.

In some embodiments, implant 12 is positioned in prepared vertebral space S between vertebrae V, as described herein, with implant 12 being free of agents, such as, for example, bone graft. That is, no agents are packed, coated or otherwise disposed on or about the surfaces of implant 12 when implant 12 is positioned between vertebrae V. Implant 12 may be positioned between vertebrae V such that surfaces 156, 174 face endplate surface E1 of vertebra V1 and surfaces 160, 178 face endplate surface E2 of vertebra V2.

In some embodiments, the inserter is rotated to cause axial translation of body 14 relative to body 70 to expand implant 12, in a direction shown by arrow B in FIG. 14. In one embodiment, the inserter is rotated in an opposite direction to drive body 14 in a second axial direction, as shown by arrow BB in FIG. 14, and cause axial translation of body 14 relative to body 70 to contract and/or collapse implant 12 from the expanded configuration. In some embodiments, implant 12 may be contracted or expanded until implant 12 engages and spaces apart opposing endplate surfaces E1, E2 and is secured within vertebral space S to stabilize and immobilize portions of vertebrae V in connection with bone growth for fusion and fixation of vertebrae V1, V2. Fixation of implant 12 with endplate surfaces E1, E2 may be facilitated by the resistance provided by the joint space and/or engagement with endplate surfaces E1, E2. In some embodiments, implant 12 may engage only one of endplate surfaces E1, E2. Once implant 12 is manipulated to have a selected height, setscrew 128 is rotated to fix body 14 relative to body 70 to fix the height of implant 12 at the selected height.

Figure 20:
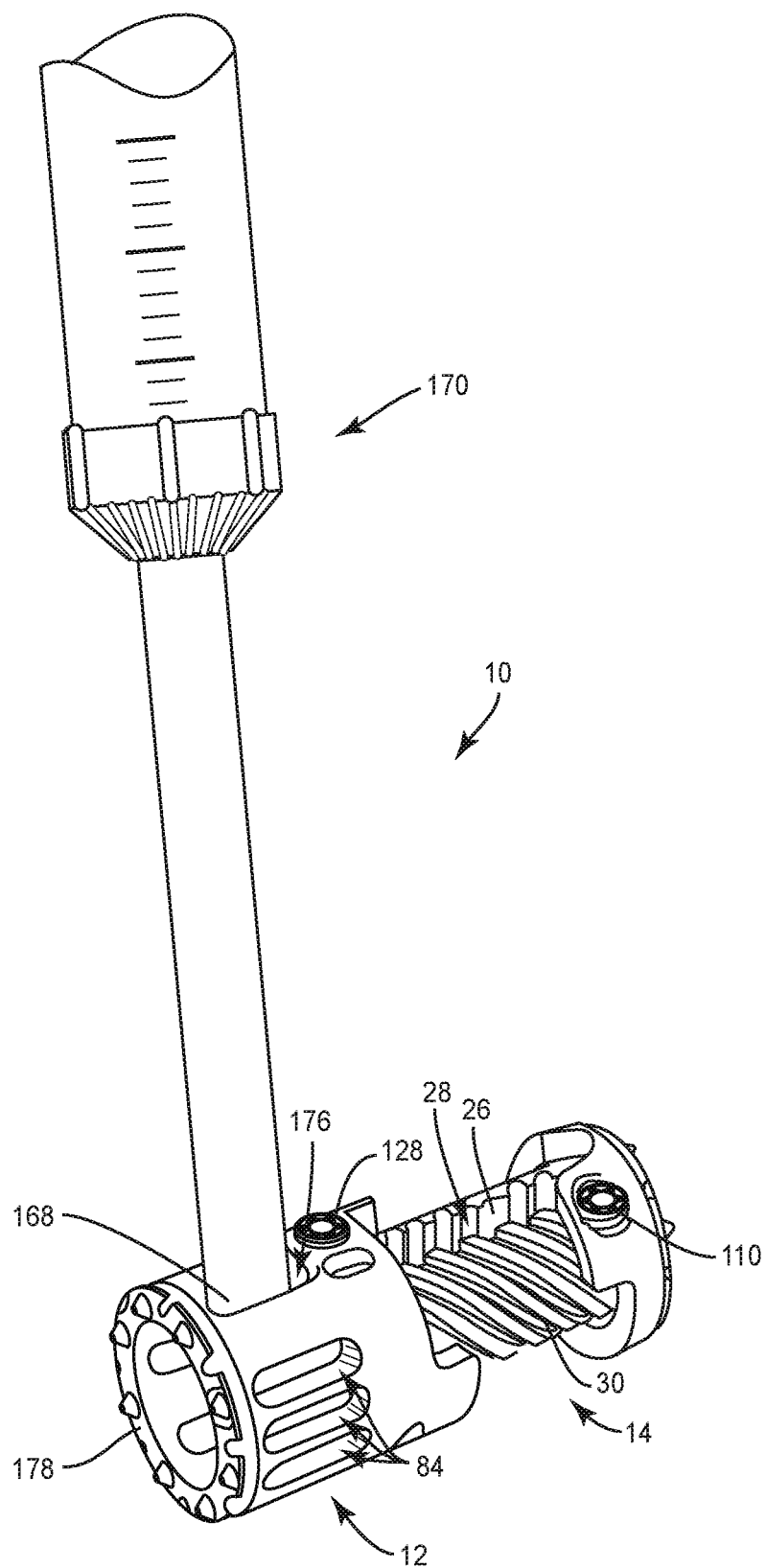
FIG. 20 is a perspective view of components of one embodiment of a surgical system in accordance with the principles of the present disclosure disposed with vertebrae.

After the height of implant 12 is fixed at the selected height, tip 168 of syringe 170 is inserted into opening 82, as shown in FIG. 20, and bone graft, such as, for example, autograft and/or allograft is injected through opening 84 and into cavity 80 using syringe 170 to at least partially fill cavity 80. In some embodiments, bone graft is injected through opening 84 and into cavity 80 using syringe 170 to completely fill cavity 80. In some embodiments, bone graft that has been injected into cavity 80 will migrate through opening 172 and/or opening 176 such that some bone graft will exit cavity 82 through opening 172 and/or opening 176 to promote fusion of vertebrae V. In some embodiments, the bone graft comprises cortical demineralized bone fibers, demineralized bone particles (≥90≥1200 μm in diameter), mineralized cortical/cancellous chips, or a combination thereof. In some embodiments, the bone graft is hydrated with either saline, blood, bone marrow, etc. to provide a flowable mixture that can be delivered via injection into the cavity during pre- and/or post-implantation.

Tip 164 of syringe 166 is inserted into one of openings 162, 162a, as shown in FIG. 21, and bone graft, such as, for example, autograft and/or allograft is injected through one of openings 162, 162a and into passageway 152 using syringe 166 to at least partially fill passageway 152. In some embodiments, bone graft is injected through one of openings 162, 162a and into passageway 152 using syringe 166 to completely fill passageway 152. In some embodiments, bone graft that has been injected into passageway 152 will migrate through opening 154 such that some bone graft will exit passageway 152 through opening 154 to promote fusion of vertebrae V. In some embodiments, bone graft that has been injected into passageway 152 will migrate through opening 158 such that some bone graft will exit passageway 152 through opening 158 and flow into cavity 80.

In some embodiments, bone graft is injected through opening 84 and into cavity 80 and through one of openings 162, 162a and into passageway 152 until implant 12 is completely filled with bone graft. In some embodiments, bone graft is injected through opening 84 and into cavity 80 before bone graft is injected through one of openings 162, 162a and into passageway. In some embodiments, bone graft is injected through opening 84 and into cavity 80 after bone graft is injected through one of openings 162, 162a and into passageway. In some embodiments, bone graft is injected through opening 84 and into cavity 80 at the same time that bone graft is injected through one of openings 162, 162a and into passageway.

In some embodiments, all or a portion of at least one of slots 84, holes 162, or hole 82 extend transverse to axis A1, such as, for example, an acute angle relative to axis A1 to intentionally direct graft in a desired direction, or intentionally cause the graft to flow away from some area. For example, in some embodiments, all or a portion of at least one of slots 84, holes 162, or hole 82 can be angled toward end 16 and/or end 18 to direct graft towards the endplates of the adjacent vertebral bodies to ensure graft abuts those surfaces. The directionality of the holes could also direct graft into small spaces first that wouldn't necessarily get filled such that those small spaces get filled without restricting graft from filling the larger spaces after the small spaces have been filled. In some embodiments, at least one of cavities 150, 172 includes internal baffles to intentionally direct graft within the implant toward a selected portion of a patient's anatomy, for example.

In some embodiments, column 14, body 70, or the entire implant 12 is positioned in a bag to allow pressurization of graft to maximize filling of the voids. In some embodiments, the bag comprises a mesh. In some embodiments, the bag is integrally formed with implant 12. In some embodiments, the bag is assembled with implant 12 by surgical staff. It is envisioned that this will allow the surgeons a choice to have a tight, close or loose bag, for example. In some embodiments, the bag is assembled with implant 12 in situ. In some embodiments, the bag is continuous along the circumference, of implant 12 without covering openings 154, 158 in order to force graft to be pressed against the endplates of the surrounding vertebral bodies. In some embodiments, the bag is configured to prevent graft loss out any of the external openings of any of the components, ensuring only implant 12 is filled with graft to avoid graft from migrating into the space surrounding implant 12. As with many graft materials, they are mixed with a carrier (glycerol, water, etc). Accordingly, in some embodiments, the bag is permeable for the carrier to allow graft to flow into the voids aided by the carrier, but then when compacted the carrier would leach out, maximizing the graft that remains. That is, instead of the carrier remaining between fibers or particles of graft, the graft could be packed tightly against itself. In some embodiments, the bag is non-biodegradable and/or non-resorbable for fusion procedures of extended durations or provide strength to the bag. In some embodiments, the bag is biodegradable and/or resorbable to avoid the bag from getting in the way of bone growth and/or release one or more biologics and/or active pharmaceutical ingredients as the bag degrades/resorbs. In some embodiments, the bag is hydrophilic such that if the graft material requires a certain amount of hydration, possibly to keep adjacent fibers far enough apart to allow bone to integrate, it would be fully hydrated. In some embodiments, mesh or impermeable membranes are placed over one or more of the openings of implant 12, or fill one or more of the openings of implant 12 to prevent unwanted migration of the graft outside of implant 12.

In some embodiments, the syringe fills implant 12 with graft using the same access point as the inserter and deployment device. In some embodiments, implant 12 could be filled with graft from a different surgical access point. For example, in some embodiments, the inserter and driver could require a certain amount of removed material for their access, such that adding any additional perforations may make implant 12 too weak. By adding graft injection ports in a different orientation than the inserter access point, both a large window for grafting through is achieved, while providing adequate strength to implant 12 for bearing surgical loads. In some embodiments, the syringe delivers a desired amount of graft into implant 12 and then the graft could be packed into and/or onto implant 12 with another instrument to ensure implant 12 is fully filled.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of treating a spine, the method comprising the steps of:
    implanting a spinal implant within a patient, the spinal implant comprising:
        a first member comprising a first wall comprising opposite inner and outer surfaces, the first member comprising a first opening extending through the surfaces and a groove extending into the inner surface, the inner surface defining an axial passageway, the first opening being in communication with the axial passageway, the outer surface defining a maximum most diameter of the spinal implant,
        a second member having a proximal end and an opposite distal end positioned entirely within the axial passageway, the second member including a second wall defining an axial cavity that is coaxial with the axial passageway, the second wall defining a second opening in communication with the axial cavity, and
        a third member positioned in the groove and between the first and second members such that the first member is spaced apart from the second member by the third member; and
    injecting bone graft through the first opening and into the axial passageway and through the second opening and into the axial cavity after the spinal implant is implanted within the patient,
    wherein the second member includes an outer surface comprising a helical gear having a plurality of helical teeth, the second member including a slot that extends into the outer surface of the second member, the slot including a gear rack having a plurality of gear teeth, the third member being positioned within the groove such that teeth on the third member engage the helical teeth, the method comprising rotating the third member relative to the second member and the first member to translate the second member relative to the first member axially to move the spinal implant from a contracted configuration to an expanded configuration.

2. A method as recited in claim 1, wherein the spinal implant is free of bone graft prior to being implanted within the patient.

3. A method as recited in claim 2, wherein injecting bone graft comprises completely filling the axial passageway and the axial cavity with bone graft.

4. A method as recited in claim 2, wherein the spinal implant moves from the contracted configuration to the expanded configuration within the patient prior to injecting the bone graft into the spinal implant.

5. A method as recited in claim 2, wherein implanting the spinal implant comprises positioning the spinal implant between adjacent vertebrae, the method further comprising translating the first and second members axially to move the spinal implant from the contracted configuration to the expanded configuration such that the implant engages endplates of the vertebrae prior to injecting the bone graft into the spinal implant.

6. A method as recited in claim 2, wherein:
    the spinal implant comprises a cap having an inner surface that engages the first member such that the cap is rotatable relative to the first member, the cap defining a transverse cavity;
    the spinal implant includes a part disposed in the transverse cavity; and
    the method further comprises:
        rotating the cap relative to the first member to dispose the cap at a selected angle, and
        engaging the part with the first member to fix the cap relative to the first member at the selected angle.

7. A method as recited in claim 2, wherein injecting bone graft comprises positioning a tip of a delivery instrument into the first opening and injecting bone graft through the first opening and into the axial passageway and positioning the tip in the second opening and injecting bone graft through the second opening and into the axial cavity.

8. A method as recited in claim 7, wherein the tip has a specific size and shape that matches a size and shape of the first opening.

9. A method as recited in claim 2, wherein injecting bone graft comprises positioning a tip of a first delivery instrument into the first opening and injecting bone graft through the first opening and into the axial passageway and positioning a tip of a second delivery instrument in the second opening and injecting bone graft through the second opening and into the axial cavity.

10. A method as recited in claim 9, wherein the first opening has a size and shape that matches a size and shape of the tip of the first delivery instrument and the second opening has a size and shape that matches a size and shape of the tip of the second delivery instrument.

11. A method of treating a spine, the method comprising the steps of:
    implanting a spinal implant within a patient, the spinal implant comprising:
        an outer body comprising opposite inner and outer surfaces, the outer body comprising a first port extending through the surfaces and a circumferential groove extending into the inner surface, the inner surface defining an axial cavity in communication with the axial cavity, the outer surface defining a maximum most diameter of the spinal implant, an inner body having a proximal end and an opposite distal end positioned entirely within the axial cavity, the inner body defining an axial passageway that is coaxial with the axial cavity, the inner body defining a second port in communication with the axial passageway, and a band positioned in the groove and between the outer body and the inner body such that the band spaces the inner body apart from the outer body; and injecting bone graft through the first port and into the axial cavity and through the second port and into the axial passageway after the spinal implant is implanted within the patient, wherein the spinal implant is free of bone graft prior to being implanted within the patient, and wherein the inner body includes an outer surface comprising a helical gear having a plurality of helical teeth, the inner body including a slot that extends into the outer surface of the inner body, the slot including a gear rack having a plurality of gear teeth, the band being positioned within the groove such that teeth of the band engage the helical teeth, the method comprising rotating the band relative to the inner body and the outer body to translate the inner body relative to the outer body axially to move the spinal implant from a contracted configuration to an expanded configuration.

12. A method as recited in claim 11, wherein injecting bone graft comprises completely filling the axial cavity and the axial passageway with bone graft.

13. A method as recited in claim 11, wherein the spinal implant moves from the contracted configuration to the expanded configuration within the patient prior to injecting the bone graft into the spinal implant.

14. A method as recited in claim 11, wherein implanting the spinal implant comprises positioning the spinal implant between adjacent vertebrae, the method further comprising translating the inner body axially relative to the outer body to move the spinal implant from the contracted configuration to the expanded configuration such that the implant engages endplates of the vertebrae prior to injecting the bone graft into the spinal implant.

15. A method as recited in claim 11, wherein injecting bone graft comprises positioning a tip of a delivery instrument into the first port and injecting bone graft through the first port and into the axial cavity and positioning the tip in the second port and injecting bone graft through the second port and into the axial passageway.

16. A method as recited in claim 15, wherein the outer body is monolithic.

17. A method as recited in claim 11, wherein injecting bone graft comprises positioning a tip of a first delivery instrument into the first port and injecting bone graft through the first port and into the axial cavity and positioning a tip of a second delivery instrument in the second port and injecting bone graft through the second port and into the axial passageway.

18. A method as recited in claim 17, wherein the first port has a diameter that matches a diameter of the tip of the first delivery instrument and the second port has a diameter that matches a diameter of the tip of the second delivery instrument.

19. A method of treating a spine, the method comprising the steps of:

implanting a spinal implant within a patient, the spinal implant comprising:

a monolithic outer body comprising opposite inner and outer surfaces, the outer body comprising a first port extending through the surfaces and a circumferential groove extending into the inner surface, the inner surface defining an axial cavity extending through opposite top and bottom end surfaces of the outer body, the first port being in communication with the axial cavity, the outer surface defining a maximum most diameter of the spinal implant, an inner body having a proximal end and an opposite distal end positioned entirely within the axial cavity, the inner body defining an axial passageway that is coaxial with the axial cavity, the inner body defining a second port in communication with the axial passageway, a band positioned in the groove and between the outer body and the inner body such that an inner surface of the band directly engages the inner body and an opposite outer surface of the band directly engages the outer body to space the inner body apart from the outer body, and a cap that removably engages the inner body such that the cap is rotatable relative to the inner body, the cap defining an axial channel extending through opposite top and bottom end surfaces of the cap; and injecting bone graft into the spinal implant by positioning a tip of a first delivery instrument into the first port and injecting bone graft through the first port and into the axial cavity and positioning a tip of a second delivery instrument in the second port and injecting bone graft through the second port and into the axial passageway, wherein the first port has a diameter that matches a diameter of the tip of the first delivery instrument and the second port has a diameter that matches a diameter of the tip of the second delivery instrument, and wherein the spinal implant is free of bone graft prior to being implanted within the patient.

* * * * *